(12) United States Patent
Wyss et al.

(10) Patent No.: US 9,204,968 B2
(45) Date of Patent: *Dec. 8, 2015

(54) POSTERIOR STABILIZED ORTHOPAEDIC PROSTHESIS

(71) Applicant: DePuy (Ireland), Cork (IE)

(72) Inventors: Joseph G. Wyss, Fort Wayne, IN (US); Travis D. Bennett, Huntington, IN (US)

(73) Assignee: DEPUY (IRELAND) (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,535

(22) Filed: Apr. 21, 2014

(65) Prior Publication Data

US 2014/0228965 A1 Aug. 14, 2014

Related U.S. Application Data

(63) Continuation of application No. 13/527,758, filed on Jun. 20, 2012, now Pat. No. 8,734,522, which is a continuation of application No. 12/165,582, filed on Jun. 30, 2008, now Pat. No. 8,206,451.

(51) Int. Cl.
*A61F 2/38* (2006.01)
(52) U.S. Cl.
CPC ............. *A61F 2/3886* (2013.01); *A61F 2/3836* (2013.01); *A61F 2/3868* (2013.01)
(58) Field of Classification Search
CPC .................................................... A61F 2/3886
USPC ........................................... 623/20.14–20.32
See application file for complete search history.

(56) References Cited

U.S. PATENT DOCUMENTS

| | | |
|---|---|---|
| 3,765,033 A | 10/1973 | Goldberg et al. |
| 3,840,905 A | 10/1974 | Deane |
| 3,852,045 A | 12/1974 | Wheeler |
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |

(Continued)

FOREIGN PATENT DOCUMENTS

| | | |
|---|---|---|
| CN | 1803106 A | 7/2006 |
| CN | 1872009 A | 12/2006 |

(Continued)

OTHER PUBLICATIONS

State Intellectual Property Office of People's Republic of China; Chinese Search Report; Application No. 200910166935.6; Mar. 26, 2013, 2 pages.

(Continued)

*Primary Examiner* — David H Willse
*Assistant Examiner* — Javier Blanco
(74) *Attorney, Agent, or Firm* — Barnes & Thornburg, LLP

(57) ABSTRACT

A posterior stabilized knee orthopaedic prosthesis includes a tibial bearing and a femoral component configured to articulate with the tibial bearing. The tibial bearing includes a spine having a concave cam surface and a convex cam surface. The femoral component includes a posterior cam having a concave cam surface and a convex cam surface. During flexion, the concave cam surface of the posterior cam contacts the convex cam surface of the spine and the convex cam surface of the posterior cam contacts the concave cam surface of the spine.

12 Claims, 12 Drawing Sheets

(56) References Cited

U.S. PATENT DOCUMENTS

| | | |
|---|---|---|
| 4,206,516 A | 6/1980 | Pilliar |
| 4,209,861 A | 7/1980 | Walker et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,340,978 A | 7/1982 | Buechel et al. |
| 4,470,158 A | 9/1984 | Pappas et al. |
| 4,612,160 A | 9/1986 | Donlevy |
| 4,673,407 A | 6/1987 | Martin |
| 4,714,474 A | 12/1987 | Brooks, Jr. |
| 4,795,468 A | 1/1989 | Hodorek |
| 4,808,185 A | 2/1989 | Penenberg et al. |
| 4,822,362 A | 4/1989 | Walker |
| 4,838,891 A | 6/1989 | Branemark |
| 4,888,021 A | 12/1989 | Forte et al. |
| 4,938,769 A | 7/1990 | Shaw |
| 4,944,757 A | 7/1990 | Martinez |
| 4,944,760 A | 7/1990 | Kenna |
| 4,950,298 A | 8/1990 | Gustilo et al. |
| 4,963,152 A | 10/1990 | Hofmann et al. |
| 4,990,163 A | 2/1991 | Ducheyne |
| 5,007,933 A | 4/1991 | Sidebotham et al. |
| 5,011,496 A | 4/1991 | Forte et al. |
| 5,019,103 A | 5/1991 | Van Zile |
| 5,037,423 A | 8/1991 | Kenna |
| 5,071,438 A | 12/1991 | Jones et al. |
| 5,080,675 A | 1/1992 | Lawes |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,147,405 A | 9/1992 | Van Zile et al. |
| 5,171,283 A | 12/1992 | Pappas |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin |
| 5,258,044 A | 11/1993 | Lee |
| 5,271,737 A | 12/1993 | Baldwin |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker |
| 5,330,534 A | 7/1994 | Herrington et al. |
| 5,344,460 A | 9/1994 | Turanyi et al. |
| 5,344,461 A | 9/1994 | Phlipot |
| 5,344,494 A | 9/1994 | Davidson |
| 5,358,527 A | 10/1994 | Forte |
| 5,368,881 A | 11/1994 | Kelman |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun |
| 5,449,745 A | 9/1995 | Sun |
| 5,458,637 A | 10/1995 | Hayes |
| 5,480,446 A | 1/1996 | Goodfellow |
| 5,543,471 A | 8/1996 | Sun |
| 5,549,686 A | 8/1996 | Johnson et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun |
| 5,658,333 A | 8/1997 | Kelman |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier |
| 5,702,464 A | 12/1997 | Lackey et al. |
| 5,702,466 A | 12/1997 | Pappas et al. |
| 5,725,584 A | 3/1998 | Walker et al. |
| 5,728,748 A | 3/1998 | Sun |
| 5,732,469 A | 3/1998 | Hamamoto |
| 5,755,800 A | 5/1998 | O'Neil |
| 5,755,801 A | 5/1998 | Walker et al. |
| 5,755,803 A | 5/1998 | Haines et al. |
| 5,765,095 A | 6/1998 | Flak |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow |
| 5,871,546 A | 2/1999 | Colleran et al. |
| 5,879,394 A | 3/1999 | Ashby |
| 5,879,400 A | 3/1999 | Merrill |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman |
| 5,964,808 A | 10/1999 | Blaha |
| 5,976,147 A | 11/1999 | LaSalle et al. |
| 5,984,969 A | 11/1999 | Matthews |
| 5,989,027 A | 11/1999 | Wagner |
| 5,997,577 A | 12/1999 | Herrington et al. |
| 6,004,351 A | 12/1999 | Tomita et al. |
| 6,005,018 A | 12/1999 | Cicierega |
| 6,010,534 A | 1/2000 | O'Neil et al. |
| 6,013,103 A | 1/2000 | Kaufman et al. |
| 6,017,975 A | 1/2000 | Saum |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal Or |
| 6,068,658 A | 5/2000 | Insall |
| 6,080,195 A | 6/2000 | Colleran et al. |
| 6,090,144 A | 7/2000 | Letot |
| 6,123,728 A | 9/2000 | Brosnahan et al. |
| 6,123,729 A | 9/2000 | Insall et al. |
| 6,123,896 A | 9/2000 | Meeks, III |
| 6,126,692 A | 10/2000 | Robie et al. |
| 6,135,857 A | 10/2000 | Shaw |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun |
| 6,206,926 B1 | 3/2001 | Pappas |
| 6,210,444 B1 | 4/2001 | Webster |
| 6,210,445 B1 | 4/2001 | Zawadzki |
| 6,217,618 B1 | 4/2001 | Hileman |
| 6,228,900 B1 | 5/2001 | Shen |
| 6,238,434 B1 | 5/2001 | Pappas |
| 6,242,507 B1 | 6/2001 | Saum |
| 6,245,276 B1 | 6/2001 | McNulty |
| 6,258,127 B1 | 7/2001 | Schmotzer |
| 6,264,697 B1 | 7/2001 | Walker |
| 6,280,476 B1 | 8/2001 | Metzger |
| 6,281,264 B1 | 8/2001 | Salovey |
| 6,299,646 B1 | 10/2001 | Chambat et al. |
| 6,316,158 B1 | 11/2001 | Saum |
| 6,319,283 B1 | 11/2001 | Insall |
| 6,325,828 B1 | 12/2001 | Dennis et al. |
| 6,344,059 B1 | 2/2002 | Krakovits et al. |
| 6,361,564 B1 | 3/2002 | Marceaux |
| 6,372,814 B1 | 4/2002 | Sun |
| 6,379,388 B1 | 4/2002 | Ensign et al. |
| 6,428,577 B1 | 8/2002 | Evans et al. |
| 6,443,991 B1 | 9/2002 | Running |
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |

(56) References Cited

U.S. PATENT DOCUMENTS

| | | |
|---|---|---|
| 6,506,215 B1 | 1/2003 | Letot |
| 6,506,216 B1 | 1/2003 | McCue |
| 6,524,522 B2 | 2/2003 | Vaidyanathan |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee |
| 6,589,283 B1 | 7/2003 | Metzger et al. |
| 6,592,787 B2 | 7/2003 | Pickrell |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre |
| 6,664,308 B2 | 12/2003 | Sun |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun |
| 6,846,327 B2 | 1/2005 | Khandkar |
| 6,846,329 B2 | 1/2005 | McMinn |
| 6,849,230 B1 | 2/2005 | Feichtinger |
| 6,852,272 B2 | 2/2005 | Artz |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram |
| 7,160,330 B2 | 1/2007 | Axelson, Jr. et al. |
| 7,175,665 B2 | 2/2007 | German |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burseein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 8,187,335 B2 | 5/2012 | Wyss et al. |
| 8,192,498 B2 | 6/2012 | Wagner et al. |
| 8,784,496 B2 | 7/2014 | Wagner et al. |
| 8,795,380 B2 | 8/2014 | Heldreth et al. |
| 8,828,086 B2 | 9/2014 | Williams et al. |
| 8,834,575 B2 | 9/2014 | Wyss et al. |
| 2002/0138150 A1 | 9/2002 | Leclercq |
| 2003/0009232 A1 | 1/2003 | Metzger et al. |
| 2003/0035747 A1 | 2/2003 | Anderson |
| 2003/0044301 A1 | 3/2003 | Lefebvre |
| 2003/0075013 A1 | 4/2003 | Grohowski |
| 2003/0139817 A1 | 7/2003 | Tuke |
| 2003/0153981 A1 | 8/2003 | Wang |
| 2003/0171820 A1 | 9/2003 | Wilshaw |
| 2003/0199985 A1 | 10/2003 | Masini |
| 2003/0212161 A1 | 11/2003 | McKellop |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen |
| 2004/0186583 A1 | 9/2004 | Keller |
| 2004/0215345 A1 | 10/2004 | Perrone |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier |
| 2005/0059750 A1 | 3/2005 | Sun |
| 2005/0069629 A1 | 3/2005 | Becker |
| 2005/0096747 A1 | 5/2005 | Tuttle et al. |
| 2005/0100578 A1 | 5/2005 | Schmid |
| 2005/0123672 A1 | 6/2005 | Justin |
| 2005/0143832 A1 | 6/2005 | Carson |
| 2005/0154472 A1 | 7/2005 | Afriat |
| 2005/0203631 A1 | 9/2005 | Daniels |
| 2005/0209701 A1 | 9/2005 | Suguro et al. |
| 2005/0209702 A1 | 9/2005 | Todd |
| 2005/0249625 A1 | 11/2005 | Bram |
| 2005/0278035 A1 | 12/2005 | Wyss et al. |
| 2006/0002810 A1 | 1/2006 | Grohowski |
| 2006/0015185 A1 | 1/2006 | Chambat et al. |
| 2006/0036329 A1 | 2/2006 | Webster |
| 2006/0052875 A1 | 3/2006 | Bernero |
| 2006/0100714 A1 | 5/2006 | Ensign |
| 2006/0178749 A1 | 8/2006 | Pendleton et al. |
| 2006/0195195 A1 | 8/2006 | Burstein |
| 2006/0228247 A1 | 10/2006 | Grohowski |
| 2006/0231402 A1 | 10/2006 | Clasen |
| 2006/0241781 A1 | 10/2006 | Brown |
| 2006/0257358 A1 | 11/2006 | Wen |
| 2006/0271191 A1 | 11/2006 | Hermansson |
| 2006/0289388 A1 | 12/2006 | Yang |
| 2007/0061014 A1 | 3/2007 | Naegerl |
| 2007/0073409 A1 | 3/2007 | Cooney |
| 2007/0078521 A1 | 4/2007 | Overholser |
| 2007/0100463 A1 | 5/2007 | Aram |
| 2007/0129809 A1 | 6/2007 | Meridew |
| 2007/0135926 A1 | 6/2007 | Walker |
| 2007/0173948 A1 | 7/2007 | Meridew |
| 2007/0196230 A1 | 8/2007 | Hamman |
| 2007/0203582 A1 | 8/2007 | Campbell |
| 2007/0219639 A1 | 9/2007 | Otto et al. |
| 2007/0293647 A1 | 12/2007 | McKellop |
| 2008/0004708 A1 | 1/2008 | Wyss |
| 2008/0021566 A1 | 1/2008 | Peters et al. |
| 2008/0091272 A1 | 4/2008 | Aram |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |

(56) References Cited

U.S. PATENT DOCUMENTS

| | | |
|---|---|---|
| 2008/0161927 A1 | 7/2008 | Savage |
| 2008/0195108 A1 | 8/2008 | Bhatnagar et al. |
| 2008/0199720 A1 | 8/2008 | Liu |
| 2008/0206297 A1 | 8/2008 | Roeder |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck |
| 2009/0084491 A1 | 4/2009 | Uthgenannt |
| 2009/0088859 A1 | 4/2009 | Hazebrouck et al. |
| 2009/0125114 A1 | 5/2009 | May et al. |
| 2009/0192610 A1 | 7/2009 | Case |
| 2009/0265012 A1 | 10/2009 | Engh et al. |
| 2009/0265013 A1 | 10/2009 | Mandell |
| 2009/0292365 A1 | 11/2009 | Smith |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu |
| 2010/0016979 A1 | 1/2010 | Wyss et al. |
| 2010/0036499 A1 | 2/2010 | Pinskerova |
| 2010/0036500 A1 | 2/2010 | Heldreth |
| 2010/0042224 A1 | 2/2010 | Otto et al. |
| 2010/0042225 A1 | 2/2010 | Shur |
| 2010/0063594 A1 | 3/2010 | Hazebrouck |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu |
| 2010/0100189 A1 | 4/2010 | Metzger |
| 2010/0100190 A1 | 4/2010 | May |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett |
| 2010/0286788 A1 | 11/2010 | Komistek |
| 2010/0292804 A1 | 11/2010 | Samuelson |
| 2010/0305710 A1 | 12/2010 | Metzger |
| 2010/0312350 A1 | 12/2010 | Bonutti |
| 2011/0029090 A1 | 2/2011 | Zannis |
| 2011/0029092 A1 | 2/2011 | Deruntz |
| 2011/0035017 A1 | 2/2011 | Deffenbaugh |
| 2011/0035018 A1 | 2/2011 | Deffenbaugh |
| 2011/0106268 A1 | 5/2011 | Deffenbaugh |
| 2011/0118847 A1 | 5/2011 | Lipman et al. |
| 2011/0125280 A1 | 5/2011 | Otto et al. |
| 2011/0153026 A1 | 6/2011 | Heggendorn et al. |
| 2012/0239158 A1 | 9/2012 | Wagner et al. |
| 2012/0259417 A1 | 10/2012 | Wyss et al. |
| 2012/0271428 A1 | 10/2012 | Heldreth et al. |
| 2012/0296437 A1 | 11/2012 | Wyss et al. |
| 2013/0006372 A1 | 1/2013 | Wyss et al. |
| 2013/0006373 A1 | 1/2013 | Wyss et al. |
| 2014/0243987 A1 | 8/2014 | Wagner et al. |
| 2014/0303740 A1 | 10/2014 | Heldreth et al. |
| 2014/0350686 A1 | 11/2014 | Williams et al. |
| 2015/0005888 A1 | 1/2015 | Wyss et al. |

FOREIGN PATENT DOCUMENTS

| | | |
|---|---|---|
| DE | 4308563 | 9/1994 |
| DE | 19529824 | 2/1997 |
| EP | 510178 | 5/1992 |
| EP | 495340 A1 | 7/1992 |
| EP | 634155 | 1/1995 |
| EP | 636352 A2 | 2/1995 |
| EP | 732091 | 9/1996 |
| EP | 883388 | 12/1998 |
| EP | 634156 | 5/1999 |
| EP | 1374805 | 1/2001 |
| EP | 1129676 | 9/2001 |
| EP | 636352 B1 | 1/2002 |
| EP | 1196118 | 4/2002 |
| EP | 765645 | 8/2003 |
| EP | 1421918 A1 | 5/2004 |
| EP | 1440675 | 7/2004 |
| EP | 1470801 | 10/2004 |
| EP | 732092 | 2/2005 |
| EP | 1518521 A2 | 3/2005 |
| EP | 1226799 | 5/2005 |
| EP | 1591082 | 11/2005 |
| EP | 1779812 A1 | 5/2007 |
| EP | 1923079 A1 | 5/2008 |
| EP | 2649965 A1 * | 10/2013 |
| FR | 2417971 | 2/1979 |
| FR | 2621243 | 4/1989 |
| FR | 2653992 A1 | 5/1991 |
| FR | 2780636 A1 | 1/2000 |
| FR | 2787012 | 6/2000 |
| FR | 2809302 A1 | 11/2001 |
| FR | 2835178 | 8/2003 |
| GB | 1065354 A | 4/1967 |
| GB | 2293109 A | 3/1996 |
| GB | 2335145 A | 9/1999 |
| JP | 62205201 A | 9/1987 |
| JP | 2004167255 | 2/1996 |
| JP | 08224263 A | 9/1996 |
| JP | 2002291779 A | 10/2002 |
| JP | 2004167255 | 6/2004 |
| JP | 2006015133 A | 1/2006 |
| WO | 7900739 | 10/1979 |
| WO | 8906947 | 8/1989 |
| WO | 9014806 A1 | 12/1990 |
| WO | 9601725 | 1/1996 |
| WO | 9623458 | 8/1996 |
| WO | 9624311 | 8/1996 |
| WO | 9624312 | 8/1996 |
| WO | 9846171 | 10/1998 |
| WO | 9927872 | 6/1999 |
| WO | 9966864 A1 | 12/1999 |
| WO | 0209624 | 2/2002 |
| WO | 03039609 A1 | 5/2003 |
| WO | 03101647 A2 | 12/2003 |
| WO | 2004058108 | 7/2004 |
| WO | 2004069104 | 8/2004 |
| WO | 2005009489 A2 | 2/2005 |
| WO | 2005009729 A2 | 2/2005 |
| WO | 2005072657 | 8/2005 |
| WO | 2005087125 | 9/2005 |
| WO | 2006014294 A1 | 2/2006 |
| WO | 2006130350 A2 | 12/2006 |
| WO | 2007106172 | 9/2007 |
| WO | 2007106172 A | 9/2007 |
| WO | 2007108804 | 9/2007 |
| WO | 2007119173 | 10/2007 |
| WO | 2008100784 A2 | 8/2008 |
| WO | 2009046212 A2 | 4/2009 |
| WO | 2009128943 A2 | 10/2009 |

OTHER PUBLICATIONS

European Search Report for European Patent Application No. 09164235.5-1526, Dec. 22, 2009, 6 pgs.

European Search Report for European Patent Application No. 09164168.8-1526, Jan. 4, 2010, 6 pgs.

European Search Report for European Patent Application No. 09164160.5-1526, Jan. 4, 2010, 4 pgs.

European Search Report for European Patent Application No. 09164228.0-1526, Feb. 2, 2010, 6 pgs.

Biomet, Vanguard Mono-Lock Tibial System, Patented Convertible Tibial Bearing Technology, 2009, 2 Pages.

Cari Zeiss, Zeiss Surfcomm 5000—"Contour and Surface Measuring Machines", 2005, 16 pages.

DePuy Inc., "AMK Total Knee System Product Brochure", 1996, 8 pages.

(56) References Cited

OTHER PUBLICATIONS

DePuy Knees International, "Sigma CR Porocoat®," 1 page.
DePuy Orthopaedics, Inc., "AMK Total Knee System Legent II Surgical Techinque", 1998, 30 pages.
DePuy Orthopaedics, Inc., "Sigma Fixed Bearing Knees—Function with Wear Resistance", 2010, 0612-65-508 (Rev. 1) 20 pages.
DePuy PFC Sigma RP, "PFC Sigma Knee System with Rotating Platform Technical Monograph", 1999, 0611-29-050 (Rev. 3), 70 pages.
Effects of Coronal Plane Conformity on Tibial Loading in TKA: A Comparison of AGC Flat Versus Conforming Articulations, Brent, et al, Orthopaedic Surgery, Surgical Technology International, XVIII, 6 pages.
European Search Report for European Patent Application No. 09164245.4-2310, Oct. 15, 2009, 5 pgs.
European Search Report for European Patent Application No. 08253140.1-2310, Dec. 23, 2008, 7 pgs.
European Search Report for European Patent Application No. 11150648.1-2310, Apr. 7, 2011, 4 pages.
European Search Report for European Patent Application No. 06739287.8-2310, Mar. 16, 2010, 3 Pages.
European Search Report for European Patent Application No. 09164478.1-2310, Oct. 20, 2009, 6 Pages.
European Search Report for European Patent Application No. 09164478.1-2310, Apr. 28, 2010, 12 Pages.
European Search Report for European Patent Application No. 10162138.1, Aug. 30, 2010, 7 Pages.
Japanese Search Report for Japanese Patent Application No. 2009-501393, Oct. 26, 2010, 5 Pages.
PCT Notification Concerning Transmittal of International Prel. Report for Corresponding International App. No. PCT/US2006/010431, Jun. 5, 2007, 89 Pages.
Procedure, References Guide for Use with P.F.C. Sigma Knee Systems, 1998, 8 pages.
Signus Medizintechnik, "PEEK-OPTIMA®, The Polymer for Implants, Technical Information for the Medical Professional", 7 pages.
The Effects of Conformity and Load in Total Knee Replacement, Kuster, et al, Clinical Orthopaedics and Related Research No. 375, Jun. 2000.
Zimmer Nexgen Trabecular Metal Tibial Tray, The Best Thing Next to Bone, 97-5954-001-00, 2007, 4 pages.
Zimmer, Trabecular Metal Monoblock Tibial Components, An Optimal Combination of Material and Design, www.zimmer.com, 2009, 3 pages.
European search report; European Application No. 10174439.9-1526; Dec. 20, 2010; 4 pages.
"Vanguard Complete Knee System," Biomet, available at: http://www.biomet.com/patients/vanguard_complete.cfm, downloaded on Feb. 2009, (3 pages).
"NexGen Complete Knee Solution Cruciate Retaining Knee (CR)," Zimmer, available at: http://zimmercom.au/ctl?template=PC&op=global&action=&template=PC&id=356, downloaded on Feb. 18, 2009, (1 page).
Scorpio Knee TS Single Axis Revision Knee System, Stryker Orthopaedics, http://www.stryker.com/stellent/groups/public/documents/web_prod/023609.pdf, (6 pages).
P. Johal et al, "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).
Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, (4 pages).
Asano et al. "In Vivo Three-Dimensional Knee Kinematics Using a Biplanar Image-Matching Technique," Clin Orthop Rel Res, 388: 157-166, 2001, (10 pages).
Kessler et al., "Sagittal curvature of total knee replacements predicts in vivo kinematics," Clinical Biomechanics 22(1): 52-58, 2007.

Wang et al., "Biomechanical differences exhibited during sit-to-stand between total knee arthroplasty designs of varying radii," J Arthroplsaty 21(8): 1196-9, 2006.
Saari et al., "The effect of tibial insert design on rising from a chair; motion analysis after total knee replacement," Clin Biomech 19(9): 951-6, 2004.
Ranawat, "Design may be counterproductive for optimizing flexion after TKR," Olin Orthop Rel Res 416: 174-6, 2003.
D'Lima et al., "Quadriceps moment arm and quadriceps forces after total knee arthroplasty," Clin Orthop Rel Res 393:213-20, 2001.
Uvehammer et al., "In vivo kinematics of total knee arthroplasty: flat compared with concave tibial joint surface," J Orthop Res 18(6): 856-64, 2000.
Dennis et al., "In vivo anteroposterior femorotibial translation of total knee arthroplasty: a multicenter analysis," Olin Orthop Rel Res, 356: 47-57, 1998.
Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.
Wang et al., "A biomechanical comparison between the single-axis and multi-axis total knee arthroplasty systems for stand-to-sit movement," Clin Biomech 20(4): 428-33, 2005.
Dennis et al., "Multicenter Determination of in Vivo Kinematics After Total Knee Arthroplasty," Clin. Orthop. Rel. Res., 416, 37-57, 21 pgs.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
Suggs et al., "Three-Dimensional Tibiofemoral Articular Contact Kinematics of a Cruciate-Retaining Total Knee Arthroplasty," JBJS-Am, vol. 88, No. 2, 2006, 10 pgs.
Dennis et al., "In Vivo Determination of Normal and Anterior Cruciate Ligament-Deficient Knee Kinematics," J. Biomechanics, 38, 241-253, 2005, 13 pgs.
Li et al., "Anterior Cruciate Ligament Deficiency Alters the In Vivo Motion of the Tibiofemoral Cartilage Contact Points in Both Anteroposterior and Mediolateral Directions," JBJS-Am, vol. 88, No. 8, Aug. 2006, 10 pgs.
Ries, "Effect of ACL Sacrifice, Retention, or Substitution on K After TKA," http://www.orthosupersite.com/view.asp?rID=23134, Aug. 2007, 5 pgs.
Ferris, "Matching observed spiral form curves to equations of spirals in 2-D images, "The First Japanese-Australian Joint Seminar, 7 pgs.
Goodfellow et al., "The Mechanics of the Knee and Prosthesis Design," The Journal of Bone and Joint Surgery, vol. 60-B, No. 3, 12 pgs.
Zimmer Nexgen Trabecular Metal Tibial Tray, "The Best Thing Next to Bone", 97-5954-001-00, 2007, 4 pages.
European Search Report for European Patent Application No. 08164944.4-2310-2042131, Mar. 16, 2009, 12 pgs.
Shaw et al., "The Longitudinal Axis of the Knee and the Role of the Cruciate Ligaments in Controlling Transverse Rotation", J. Bone Joint Surg. Am 1974:56:1603-1609, 8 pages (1974).
Kurosawa, et al., "Geometry and Motion of the Knee for Implant and Orthotic Design", The Journal of Biomechanics 18 (1985), pp. 487-499, 12 pages.
Barnes, C.L., et al, "Kneeling Is Safe for Patients Implanted With Medical-Pivot Total Knee Arthoplasty Designs, Journal of Arthoplasty", vol. 00, No. 0 2010, 1-6, 6 pages (2010).
Blaha, et al., "Kinematics of the Human Knee Using an Open Chain Cadaver Model", Clinical Orthopaedics and Related Research, vol. 410 (2003); 25-34, 10 pages.
Dennis, et al. "A Multi-Center Analysis of Axial Femorotibial Rotation After Total Knee Arthoplasty", Clinical Orthopaedics 428 (2004); 180-189, 10 pages.
Fan, Cheng-Yu, et al., "Primitive Results After Medical-Pivot Knee Arthroplasties: A Minimum 5 Year Follow-Up Study", The Journal of Arthroplasty, vol. 25, No. 3 2010, 492-496, 5 pages (2010).

(56) References Cited

OTHER PUBLICATIONS

Freeman, M.A.R., et al., "The Movement of the Normal Tibio-Femoral Joint", The Journal of Biomechanics 38 (2005) (2), pp. 197-208, 12 pgs.

Fuller, et al., "A Comparison of Lower-Extremity Skeletal Kinematics Measured Using Skin and Pin-Mounted Markers", Human Movement Science 16 (1997) 219-242, 24 pages.

Hill, et al., "Tibiofemoral Movement 2: The Loaded and Unloaded Living Knee Studied by MRI" The Journal of Bone & Joint Surgery, vol. 82-B, No. 8 (Nov. 2000), 1196-1198, 3 pages.

Karachalios, et al., "A Mid-Term Clinical Outcome Study of the Advance Medial Pivot Knee Arthroplasty", www.sciencedirect.come, The Knee 16 (2009); 484-488, 5 pages.

Komistek, et al., "In Vivo Flouroscopic Analysis of the Normal Human Knee", Clinical Orthopaedics 410 (2003): 69-81, 13 pages.

Komistek, et al., "In Vivo Polyethylene Bearing Mobility Is Maintained in Posterior Stabilized Total Knee Arthroplasty", Clinical Orthopaedics 428 (2004): 207-213, 7 pages.

Koo, et al., "The Knee Joint Center of Rotation Is Predominantly on the Lateral Side During Normal Walking", Journal of Biomechanics, vol. 41 (2008): 1269-1273, 5 pages.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 pages.

Moonot, et al., "Correlation Between the Oxford Knee and American Knee Society Scores at Mid-Term Follow-Up", The Journal of Knee Surgery, vol. 22, No. 3 (Jul. 2009), 226-230, 5 pages.

Murphy, Michael Charles, "Geometry and the Kinematics of the Normal Human Knee", Submitted to Masachusetts Institute of Technology (1990), 379 pages.

Nakagawa, et al., "Tibiofemoral Movement 3: Full Flexion of the Normal Human Knee", J.Bone Joint Surg. Am, vol. 82-B, No. 8 (2000). 1199-1200, 2 pages.

Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009), 14:754-760, 7 pages.

Shakespeare, et al., "Flexion After Total Knee Replacement. A Comparison Between the Medical Pivot Knee and a Posterior Stabilised Knee", www.sciencedirect.com, The Knee 13 (2006): 371-372, 3 pages.

Walker, et al., "Motion of a Mobile Bearing Knee Allowing Translation of Rotation", Journal of Arthroplasty 17 (2002): 11-19, 9 pages.

2nd Int'l Johnson-Elloy Knee Meeting, Mar. 1987, 9 pages.

Operative Technique, Johnson Elloy Knee System, Chas F. Thackray, Ltd., 1988, 34 pgs.

Operative Technique the Turning Point, Accord, The Johnson/Elloy Concept, Chas FL Thackray Ltd, 32 pages (1990).

Restoration of Soft Tissue Stability, Johnson, et al., Chas. F. Thackray, Ltd., 21 pages (2001).

The Accuracy of Intramedullary Alignment in Total Knee Replacement, Elloy, et al, Chas F. Thackray Ltd, 12 pages (2008).

The Turning Point, Accord, The Johnson Elloy Concept, Chas F. Thackray Ltd, 20 pages (1984).

Prosthesis and Instrumentation the Turning Point, Accord, The Johnson/Elloy Concept, Chas F. Thackray Ltd, 8 pages (1987).

Five to Eight Year Results of the Johnson/Elloy (Accord) Total Knee Arthroplasty, Johnson et al, The Journal of Arthroplasty, vol. 8, No. 1, Feb. 1993, 6 pages.

Factors Affecting the Range of Movement of Total Knee Arthroplasty, Harvey et al, The Journal of Bone and Joint Surgery, vol. 75-B, No. 6, Nov. 1993, 6 pages.

Advice Notice (NI) Mar. 2000, Defect & Investigation Centre, Mar. 13, 2000, 3 pages.

The Johnson Elloy (Accord) Total Knee Replacement, Norton et al, The Journal of Bone and Joint Surgery (BR), vol. 84, No. 6, Aug. 2002, 4 pages.

Midvatus Approach in Total Knee Arthroplasty, A Description and a Cadaveric Study Determining The Distance of the Popliteal Artery From the Patellar Margin of the Incision, Cooper et al., The Journal of Arthoplasty, vol. 14 No. 4, 1999, 4 pages.

\* cited by examiner

POSTERIOR STABILIZED ORTHOPAEDIC PROSTHESIS

This application is a continuation of U.S. Utility patent application Ser. No. 13/527,758, which was filed on Jun. 20, 2012 and was a continuation of U.S. Utility patent application Ser. No. 12/165,582 entitled "Posterior Stabilized Orthopaedic Prosthesis," which was filed on Jun. 30, 2008 and issued as U.S. Pat. No. 8,206,451 on Jun. 26, 2012. The entirety of each of those applications is incorporated herein by reference.

CROSS-REFERENCE TO RELATED U.S. PATENT APPLICATION

Cross-reference is made to U.S. Utility patent application Ser. No. 12/165,579 entitled "Orthopaedic Femoral Component Having Controlled Condylar Curvature" by John L. Williams et al., which was filed on Jun. 30, 2008; to U.S. Utility patent application Ser. No. 12/165,574 entitled "Posterior Cruciate-Retaining Orthopaedic Knee Prosthesis Having Controlled Condylar Curvature" by Christel M. Wagner, which was filed on Jun. 30, 2008 and issued as U.S. Pat. No. 8,192,498 on Jun. 5, 2012; and to U.S. Utility patent application Ser. No. 12/165,575 entitled "Posterior Stabilized Orthopaedic Knee Prosthesis Having Controlled Condylar Curvature" by Joseph G. Wyss, which was filed on Jun. 30, 2008 and issued as U.S. Pat. No. 8,187,335 on, May 29, 2012; and to U.S. Utility patent application Ser. No. 12/488,107 entitled "Orthopaedic Knee Prosthesis Having Controlled Condylar Curvature" by Mark A. Heldreth, which was filed on Jun. 19, 2009 and issued as U.S. Pat. No. 8,236,061 on Aug. 7, 2012; the entirety of each of which is incorporated herein by reference.

TECHNICAL FIELD

The present disclosure relates generally to orthopaedic prostheses, and particularly to posterior stabilized orthopaedic prostheses for use in knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. A knee prosthesis is generally designed to duplicate the natural movement of the patient's joint. However, depending on the severity of the damage to the patient's joint, orthopaedic prostheses of varying mobility may be used. For example, in some patients, the posterior cruciate ligament may be damaged, deficient, or removed during the orthopaedic surgical procedure. In such cases, a posterior stabilized knee orthopaedic prosthesis, which typically restricts or limits the posterior movement of the tibia relative to the femur, may be used.

SUMMARY

According to one aspect, a posterior stabilized knee orthopaedic prosthesis includes a tibial bearing and a femoral component. The tibial bearing may be configured to be coupled to a tibial tray and may include a platform and a spine extending upwardly from the platform. The spine may have a posterior side including a superior and an inferior cam surface. The superior cam surface may be embodied as a convex cam surface and the inferior cam surface may be embodied as a concave cam surface. The radius of curvature of the concave cam surface of the spine of the tibial bearing may be substantially equal to or different from the radius of curvature of the convex cam surface of the spine.

In some embodiments, the superior cam surface of the spine of the tibial bearing may be convexly curved in the sagittal plane. Additionally, the inferior cam surface of the spine may be concavely curved in the sagittal plane. Further, in some embodiments, the superior cam surface and the inferior cam surface of the spine may be convexly curved in the transverse plane. In such embodiments, the radius of curvature in the transverse plane of the inferior, concave cam surface of the spine may be substantially equal to or different from the radius of curvature in the transverse plane of the superior, convex cam surface of the spine.

The femoral component of the orthopaedic prosthesis may be configured to articulate with the tibial bearing. The femoral component may include a pair of spaced apart condyles defining an intracondylar notch therebetween and a posterior cam positioned in the intracondylar notch. The posterior cam may include a concave cam surface and a convex cam surface. The tibial bearing and the femoral component are configured such that the concave cam surface of the posterior cam may contact the convex cam surface of the spine during a first range of flexion and the convex cam surface of the posterior cam may contact the concave cam surface of the spine during a second range of flexion. The first range of flexion may be less than the second range of flexion in some embodiments. For example, in one particular embodiment, the first range of flexion is about 50 degrees of flexion to about 80 degrees of flexion and the second range of flexion is about 80 degrees of flexion to about 150 degrees of flexion.

In some embodiments, the spine of the tibial bearing and the posterior cam of the femoral component may each have a substantially "S"-shaped cross-sectional profile. Additionally, in some embodiments, the radius curvature of the convex cam surface of the spine may be greater than the radius of curvature of the concave cam surface of the spine. Further, in such embodiments, the radius of curvature of the concave cam surface of the posterior cam of the femoral component may be substantially greater than the radius of curvature of the convex cam surface of the posterior cam.

According to another aspect, a posterior stabilized knee orthopaedic prosthesis may include a tibial bearing configured to be coupled to a tibial tray and a femoral component configured to be coupled to a surgically-prepared surface of the distal end of a femur. The tibial bearing may include a platform and a spine extending upwardly from the platform. The spine may include a posterior superior cam surface and a posterior inferior cam surface. The posterior superior cam surface may be concave and the posterior inferior cam surface may be convex.

In some embodiments, the radius of curvature of the superior cam surface of the spine of the tibial bearing may be substantially equal to the radius of curvature of the inferior cam surface of the spine. The superior cam surface may be concavely curved in the sagittal plane. Similarly, the inferior cam surface may be convexly curved in the sagittal plane. Additionally, in some embodiments, the superior cam surface of the spine of the tibial bearing may be convexly curved in the sagittal plane and the inferior cam surface of the spine may be concavely curved in the sagittal plane. The posterior inferior cam surface and the posterior superior cam surface of the spine may also be convexly curved in the transverse plane. In such embodiments, the radius of curvature in the transverse plane of the inferior cam surface of the spine may be substantially equal to or different from the radius of curvature in the transverse plane of the convex cam surface of the spine.

The femoral component may include a posterior cam configured to articulate with the spine of the tibial bearing. The posterior cam may include a concave cam surface and a convex cam surface. In some embodiments, the spine of the tibial bearing and the posterior cam of the femoral component may each have a substantially "S"-shaped cross-sectional profile. Additionally, in some embodiments, the radius curvature of the posterior convex cam surface of the spine may be substantially greater than the radius of curvature of the posterior concave cam surface of the spine and the radius of curvature of the convex cam surface of the posterior cam of the femoral component is substantially greater than the radius of curvature of the concave cam surface of the posterior cam. The tibial bearing and the femoral component are configured such that the concave cam surface of the posterior cam articulates on the posterior convex cam surface of the spine during a first range of flexion and the convex cam surface of the posterior cam articulates on the posterior concave cam surface of the spine during a second range of flexion greater than the first range of flexion.

According to a further aspect, a posterior stabilized knee orthopaedic prosthesis may include a tibial bearing configured to be coupled to a tibial tray and a femoral component configured to be coupled to a surgically-prepared surface of the distal end of a femur. The tibial bearing may include a platform including a medial bearing surface and a lateral bearing surface. The tibial bearing may also include a spine extending upwardly from the platform between the medial bearing surface and the lateral bearing surface. The spine may include a concave cam surface and a convex cam surface.

The femoral component may include a lateral condyle configured to articulate with the lateral bearing surface of the tibial bearing, a medial condyle configured to articulate with the medial bearing surface, and a posterior cam positioned in an intracondylar notch defined between the lateral condyle and the medial condyle. The posterior cam may include a concave cam surface and a convex cam surface. The concave cam surface of the posterior cam may initially contact the convex cam surface of the spine at a first degree of flexion and the convex cam surface of the posterior cam may initially contact the concave cam surface of the spine at a second degree of flexion greater than the first degree of flexion.

BRIEF DESCRIPTION OF THE DRAWINGS

The detailed description particularly refers to the following figures, in which.

DETAILED DESCRIPTION OF THE DRAWINGS

Figure 1:
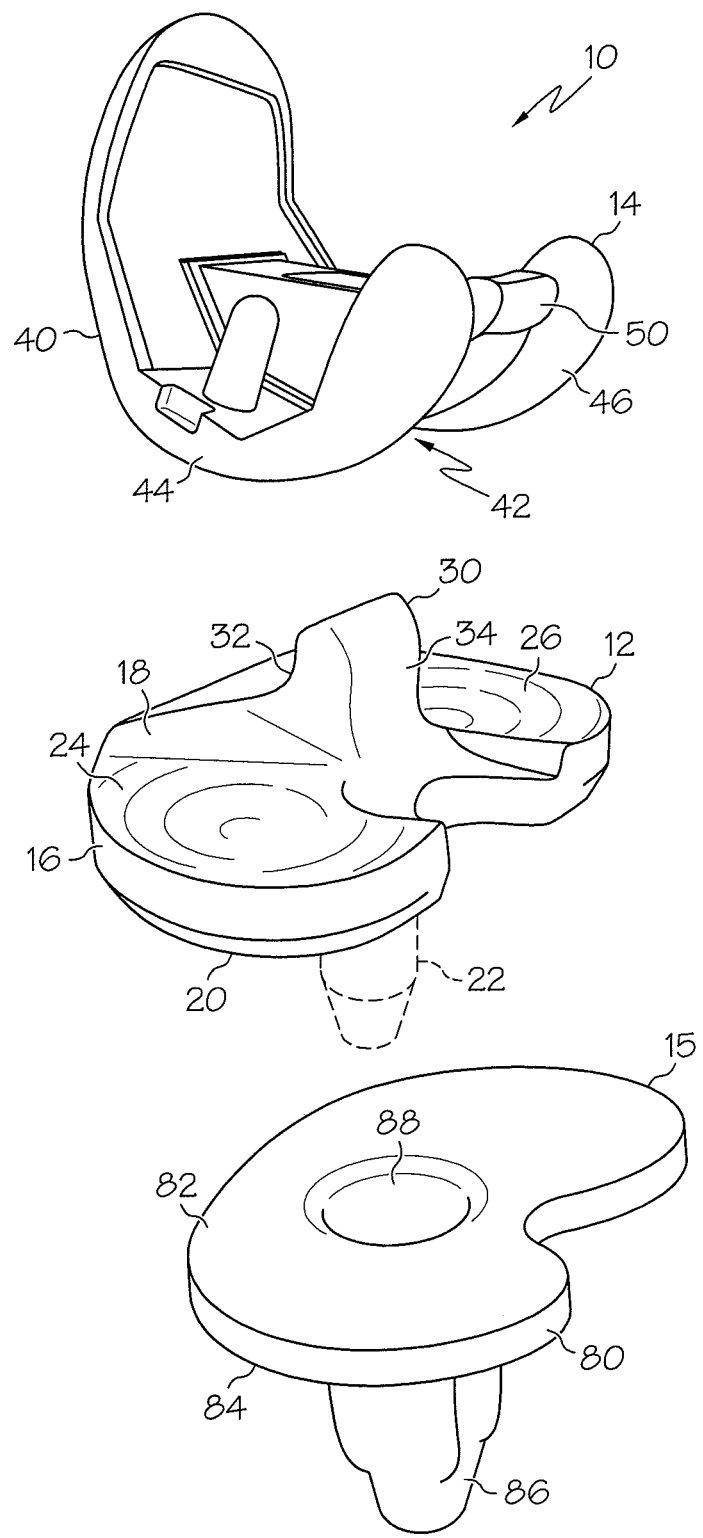
FIG. 1 is an exploded perspective view of one embodiment of an orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, in one embodiment, a posterior stabilized knee orthopaedic prosthesis 10 includes a tibial insert or bearing 12, a femoral component 14, and a tibial tray 15. The femoral component 14 is configured to articulate with the tibial bearing 12 during use. The tibial bearing 12 is illustratively formed from a polymer material such as a ultra-high molecular weight polyethylene (UHMWPE), but may be formed from other materials, such as a ceramic material, a metallic material, a bio-engineered material, or the like, in other embodiments. The femoral component 14 and the tibial tray 15 are illustratively formed from a metallic material such as cobalt-chromium or titanium, but may be formed from other materials, such as a ceramic material, a polymer material, a bio-engineered material, or the like, in other embodiments.

As discussed in more detail below, the femoral component 14 is configured to articulate with the tibial bearing 12, which is configured to be coupled with the tibial tray 15. The illustrative tibial bearing 12 is embodied as a rotating or mobile tibial bearing and is configured to rotate relative to the tibial tray 15 during use. However, in other embodiments, the tibial bearing 12 may be embodied as a fixed tibial bearing, which may be limited or restricted from rotating relative the tibial tray 15.

The tibial tray 15 is configured to be secured to a surgically-prepared proximal end of a patient's tibia (not shown). The tibial tray 15 may be secured to the patient's tibia via use of bone adhesive or other attachment means. The tibial tray 15 includes a platform 80 having an top surface 82 and a bottom surface 84. Illustratively, the top surface 82 is generally planar and, in some embodiments, may be highly polished. The tibial tray 15 also includes a stem 86 extending downwardly from the bottom surface 84 of the platform 80. A cavity or bore 88 is defined in the top surface 82 of the platform 80 and extends downwardly into the stem 86. The bore 88 is formed to receive a complimentary stem of the tibial bearing 12 as discussed in more detail below.

As discussed above, the tibial bearing 12 is configured to be coupled with the tibial tray 15. The tibial bearing 12 includes a platform 16 having an upper bearing surface 18 and a bottom surface 20. In the illustrative embodiment wherein the tibial bearing 12 is embodied as a rotating or mobile tibial bearing, the bearing 12 includes a stem 22 extending downwardly from the bottom surface 20 of the platform 16. When the tibial bearing 12 is coupled to the tibial tray 15, the stem 22 is received in the bore 88 of the tibial tray 15. In use, the tibial bearing 12 is configured to rotate about an axis defined by the stem 22 relative to the tibial tray 15. In embodiments wherein the tibial bearing 12 is embodied as a fixed tibial bearing, the bearing 12 may or may not include the stem 22 and/or may include other devices or features to secure the tibial bearing 12 to the tibial tray 15 in a non-rotating configuration.

The upper bearing surface 18 of the tibial bearing 12 includes a medial bearing surface 24, a lateral bearing surface 26, and a spine 30 extending upwardly from the platform 16. The medial and lateral bearing surfaces 24, 26 are configured to receive or otherwise contact corresponding medial and lateral condyles 44, 46 of the femoral component 14 as discussed in more detail below. As such, the bearing surfaces 24, 26 may have concave contours in some embodiments. The spine 30 is positioned between the bearing surfaces 24, 26 and includes an anterior side 32 and a posterior side 34.

The femoral component 14 is configured to be coupled to a surgically-prepared surface of the distal end of a patient's femur (not shown). The femoral component 14 may be secured to the patient's femur via use of bone adhesive or other attachment means. The femoral component 14 includes an articulating surface 40 having a pair of spaced apart medial and lateral condyles 44, 46. In use, the condyles 44, 46 replace the natural condyles of the patient's femur and are configured to articulate on the corresponding bearing surfaces 24, 26 of the platform 16 of the tibial bearing 12.

The condyles 44, 46 are spaced apart to define an intracondyle notch or recess 42 therebetween. A posterior cam 50 and an anterior cam 52 (see FIG. 2) are positioned in the intracondyle notch 42. The posterior cam 50 is located toward the posterior side of the femoral component 14 and is configured to engage or otherwise contact the spine 30 of the tibial bearing 12 during flexion as illustrated in and described in more detail below in regard to FIGS. 4-13.

Figure 2:
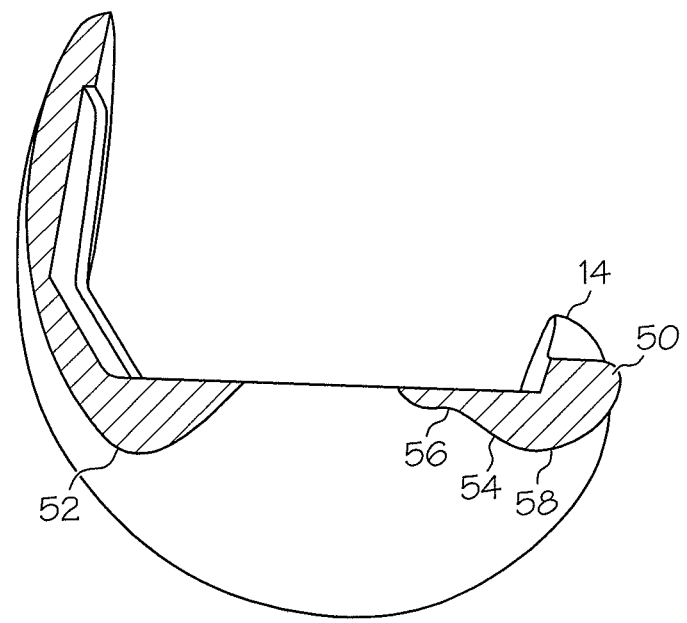
FIG. 2 is a cross-sectional view of one embodiment of a femoral component of the orthopaedic prosthesis of FIG. 1.

Referring now to FIGS. 2-5, each of the posterior cam 50 of the femoral component 14 and the spine 30 of the tibial bearing 12 have a substantially "S"-shaped cross-sectional profile in the sagittal plane. In particular, as shown in FIG. 2, the posterior cam 50 of the femoral component 14 includes a cam surface 54 configured to contact a cam surface 60 of the spine 30 during use. To do so, the cam surface 54 of the posterior cam 50 includes a concave cam surface 56 and a convex cam surface 58. In the illustrative embodiment, the convex cam surface 58 is positioned posteriorly to the concave cam surface 56. The cam surfaces 56, 58 may have similar or different radius of curvatures. For example, in some embodiments, the convex cam surface 58 may have a radius of curvature substantially larger than the radius of curvature of the concave cam surface 56. However, in other embodiments, the convex cam surface 58 may have a radius of curvature that is substantially equal to or less than the radius of curvature of the concave cam surface 56.

In some embodiments, the curvature of the cam surfaces 56, 58 may be defined by a single radius of curvature. The particular radius of curvature of the cam surfaces 56, 58 (i.e., the "size" of the cam surfaces) may be dependent upon a number of criteria such as the size of the implant, the shape or geometry of the articulating surface of the spine 30 of the tibial implant 12, and/or the like. In other embodiments, however, the concave cam surface 56 and the convex cam surface 58 of the femoral component 14 may be formed from multiple radii of curvature. For example, in the embodiment illustrated in FIG. 4, the concave cam surface 56 is defined by a radius of curvature 200 and a radius of curvature 202, each of which is tangent to the other. In one particular embodiment, the radius of curvature 200 is about 10.42 millimeters and the radius of curvature 202 is about 8.13 millimeters. Additionally, the convex cam surface 58 is defined by a plurality of radii of curvature 204, 206, 208, and 210. Each of the radii of curvature 204, 206, 208, 210 is tangent with the each adjacent radius of curvature. In one particular embodiment, the radius of curvature 204 is about 7.14 millimeters, the radius of curvature 206 is about 7.01 millimeters, the radius of curvature 208 is about 7.30 millimeters, and the radius of curvature 210 is about 2.30 millimeters. In other embodiments, a larger or lesser number of radii of curvature may be used define the cam surfaces 56, 58. Additionally, the radii of curvature 200, 202, 204, 206, 208, 210 may have other values in other embodiments.

Figure 3:
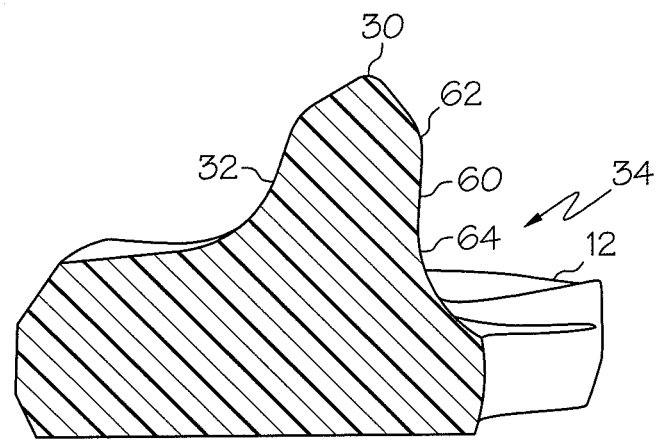
FIG. 3 is a cross-sectional view of one embodiment of a tibial bearing of the orthopaedic prosthesis of FIG. 1.
Figure 4:
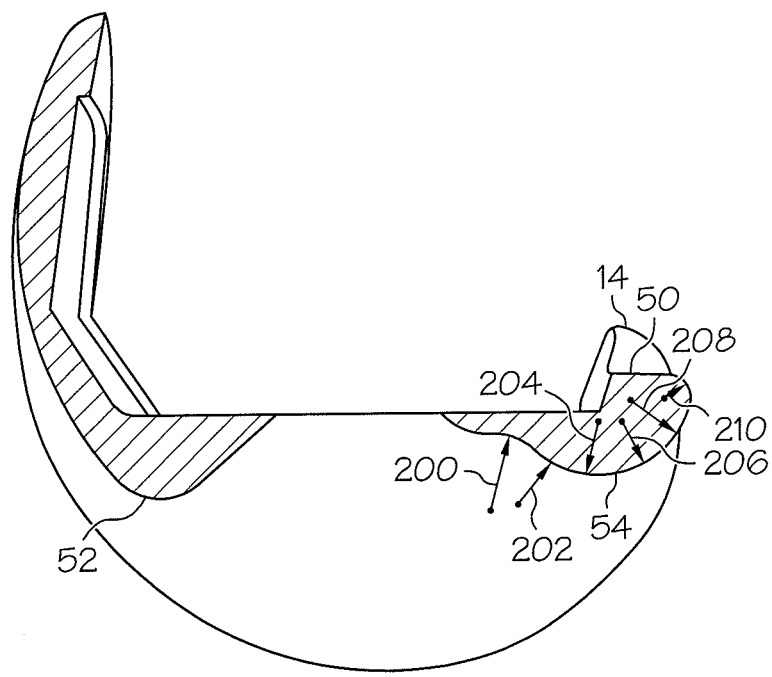
FIG. 4 is another cross-sectional view of the femoral component of FIG. 2.
Figure 5:
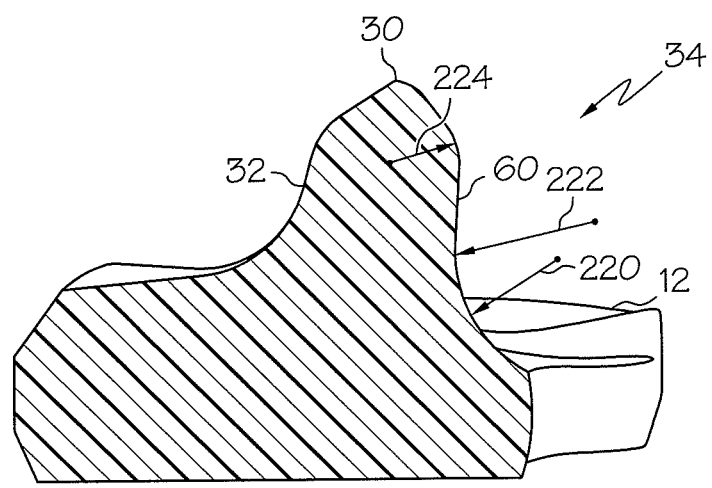
FIG. 5 is another cross-sectional view of the tibial bearing of FIG. 3.

Referring now to FIG. 3, the cam surface 60 of the tibial bearing 12 is defined on the posterior side 34 of the spine 30. Similar to the cam surface 54 of the posterior cam 50 of the femoral component 14, the cam surface 60 of the spine 30 includes a convex cam surface 62 and a concave cam surface 64. In the illustrative embodiment, the convex cam surface 62 is positioned superiorly relative to the concave cam surface 64. Similar to the cam surfaces 56, 58 of the posterior cam 50, the cam surfaces 62, 64 of the spine 30 may have similar or different radius of curvatures. For example, in some embodiments, the concave cam surface 64 has a radius of curvature substantially larger than the radius of curvature of the convex cam surface 62. However, in other embodiments, the concave cam surface 64 may have a radius of curvature that is substantially equal to or less than the radius of curvature of the convex cam surface 62.

In some embodiments, the curvature of the cam surfaces 62, 64 may be defined by a single radius of curvature. The particular radius of curvature of the cam surfaces 62, 64 (i.e., the "size" of the cam surfaces) may be dependent upon a number of criteria such as the size of the implant, the shape or geometry of the articulating surface of the posterior cam 50 of the femoral component 14, and/or the like. In other embodiments, however, the convex cam surface 62 and the concave cam surface 64 of the tibial bearing 12 may be formed from multiple radii of curvature. For example, in the embodiment illustrated in FIG. 5, the concave cam surface 64 is defined by a radius of curvature 220 and a radius of curvature 222, each of which is tangent to the other. In one particular embodiment, the radius of curvature 220 is about 9.00 millimeters and the radius of curvature 222 is about 13.00 millimeters. The convex cam surface 62 is defined by a radius of curvature 224. In one particular embodiment, the radius of curvature 224 is about 8.00 millimeters. Of course, in other embodiments, a larger or lesser number of radii of curvature may be used define the cam surfaces 62, 64. Additionally, the radii of curvature 220, 222, 224 may have other values in other embodiments.

Referring now to FIGS. 6-15, the femoral component 14 and the tibial bearing 12 are configured such that the posterior cam 50 of the femoral component 14 contacts the spine 30 of the tibial bearing 12 during flexion. In particular, during early flexion, the concave cam surface 56 of the posterior cam 50 contacts the convex cam surface 62 of the spine 30. As flexion of the orthopaedic prosthesis 10 is increased, the contact between the posterior cam 50 and the spine 30 transitions from contact between the concave cam surface 56 of the posterior cam 50 and the convex cam surface 62 of the spine 30 to contact between the convex cam surface 58 of the posterior cam 50 and the concave surface 64 of the spine 30 during late flexion.

Figure 6:
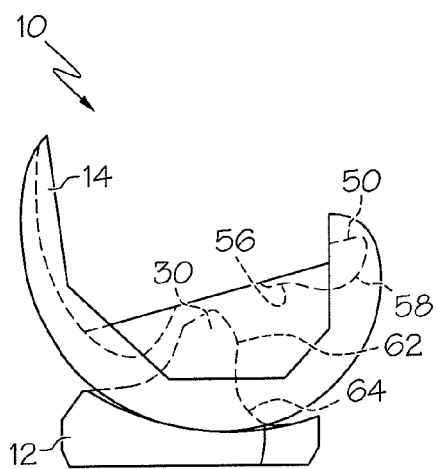
FIGS. 6-15 are side elevational views of the orthopaedic prosthesis of FIG. 1 at various degrees of flexion.
Figure 7:
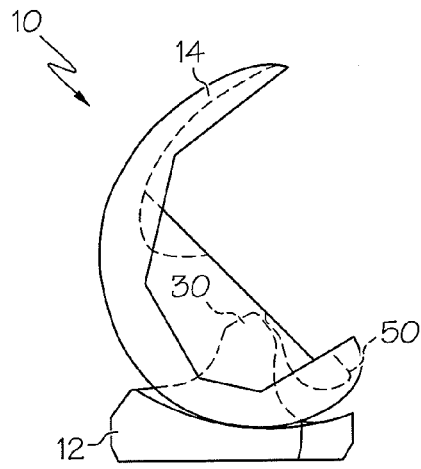
Figure 8:
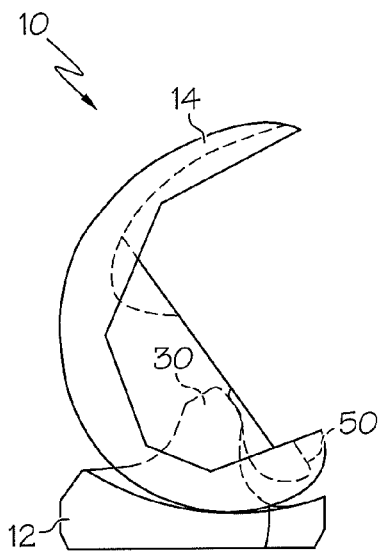

As shown in FIG. 6, when the orthopaedic prosthesis 10 is in extension or is otherwise not in flexion (e.g., a flexion of about 0 degrees), the posterior cam 50 is not in contact with the spine 30. However, during early flexion as illustrated in FIGS. 7 and 8, the posterior cam 50 of the femoral component 14 contacts the spine 30 of the tibial bearing 12. For example, in one embodiment as illustrated in FIG. 7, as the orthopaedic prosthesis 10 is moved in flexion, the concave cam surface 56 of the posterior cam 50 initially contacts the convex cam surface 62 of the spine at a predetermined degree of flexion. In the illustrative embodiment, the femoral component 14 and the tibial bearing 12 are configured such that the cam surfaces 56, 62 initially contact each other at about 60 degrees of flexion. However, in other embodiments, the degree of flexion at which initial contact between the posterior cam 50 and the spine 30 is established may be determined based on particular criteria such as the size of the orthopaedic prosthesis 10, the shape or geometry of the articulating surface of the femoral component 14 and/or the tibial bearing 12, and/or the like.

Figure 9:
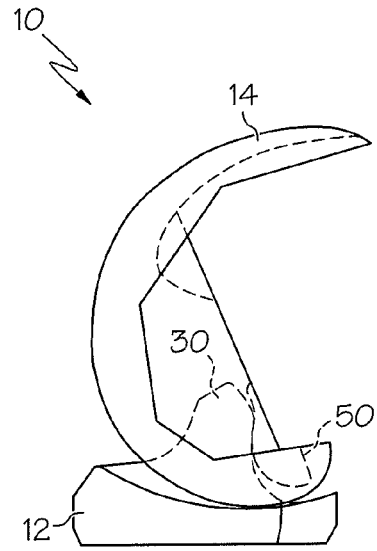
Figure 10:
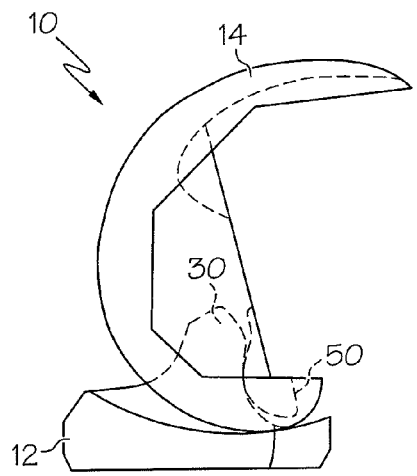
Figure 11:
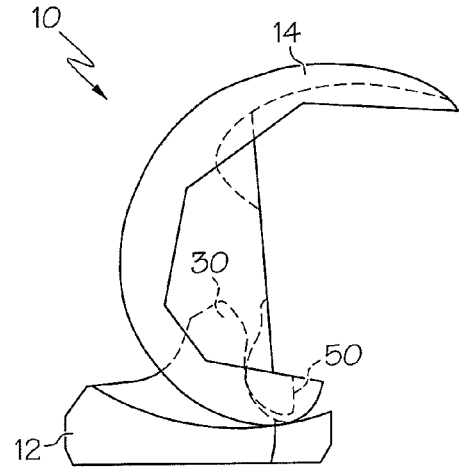
Figure 12:
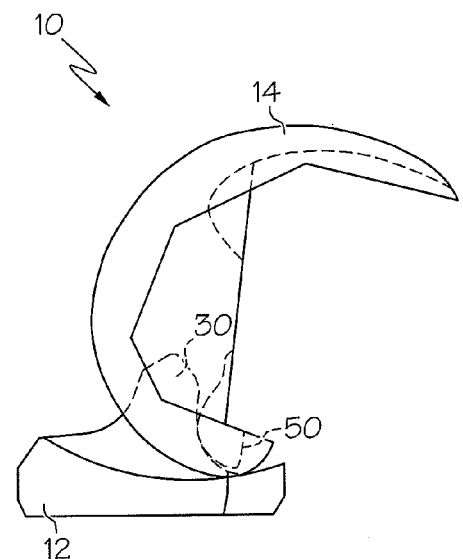
Figure 13:
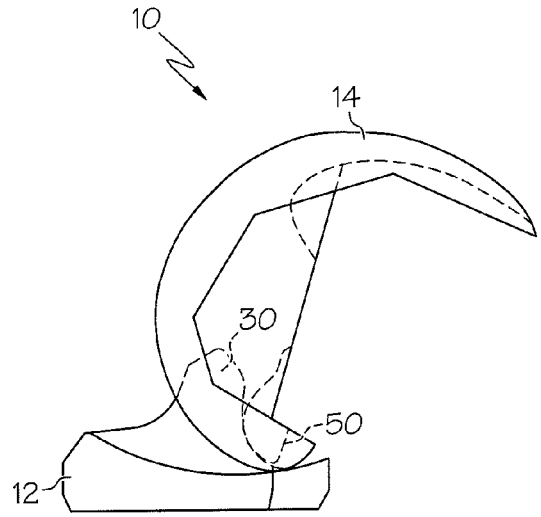
Figure 14:
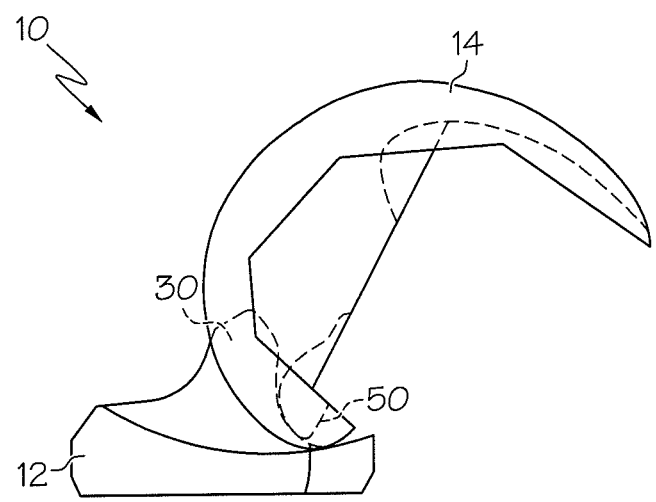
Figure 15:
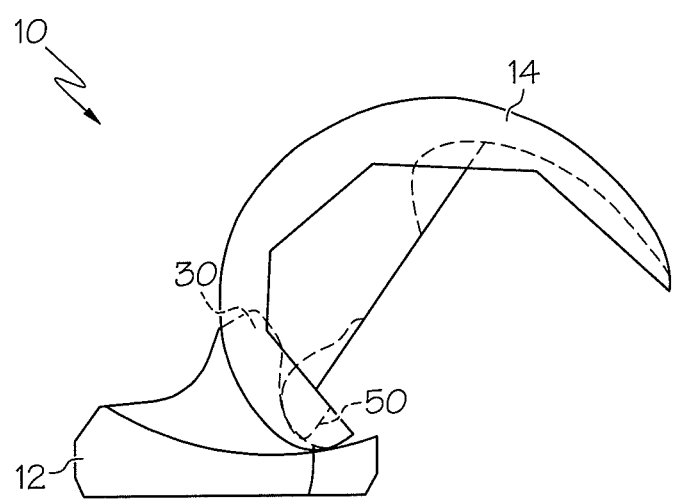

During early flexion of the orthopaedic prosthesis 10, contact between the concave cam surface 56 and the convex cam surface 62 is maintained. For example, in one embodiment as shown in FIG. 8, the convex cam surface 62 of the spine 30 may be fully "seeded" in the concave cam surface 56 of the posterior cam 50 at about 60 degrees of flexion. After early flexion, the contact between the posterior cam 50 and the spine 30 transitions from the cam surfaces 56, 62 to the cam surfaces 58, 64. For example, in one embodiment as illustrated in FIG. 9, the contact between the posterior cam 50 and the spine 30 begins transitioning to the cam surfaces 58, 64 at about 80 degrees. At this degree of flexion, initial contact between the convex cam surface 58 of the posterior cam 50 and the concave cam surface 64 of the spine 30 may be established.

During late flexion of the orthopaedic prosthesis 10, the convex cam surface 58 maintains contact with the concave cam surface 64. For example, FIGS. 10-15 illustrate one embodiment at various degrees of late flexion. In particular, the orthopaedic prosthesis 10 is illustrated at about 100 degrees of flexion in FIG. 10, at about 110 degrees of flexion in FIG. 11, at about 120 degrees of flexion in FIG. 12, at about 130 degrees of flexion in FIG. 13, at about 140 degrees of flexion in FIG. 14, and at about 150 degrees of flexion in FIG. 15.

It should be appreciated that contact between the posterior cam 50 and the spine 30 is maintained throughout the range of early and late flexion. The particular range of early flexion (i.e., the range at which the concave cam surface 56 of the posterior cam 50 contacts the convex cam surface 62 of the spine 30) and late flexion (i.e., the range at which the convex cam surface 58 of the posterior cam 50 contacts the concave cam surface 64 of the spine 30) of the orthopaedic prosthesis 10 may be dependent upon one or more criteria such as the size of the orthopaedic prosthesis 10, the shape or geometry of the articulating cam surfaces of the tibial bearing 12 and the femoral component 14, or the like. In the illustrative embodiment, the orthopaedic prosthesis 10 is configured to have an early flexion range of about 50 degrees to about 80 degrees and a late flexion range of about 80 degrees to about 150 degrees, but other ranges of flexion may be used in other embodiments. The range of early and late flexion of the orthopaedic prosthesis 10 is determined, in part, based on the radius of curvature of the cam surface 56, 58, 62, 64. As such, the range of early and late flexion of the orthopaedic prostheses 10 may be configured by adjusting the radius of curvature of the cam surfaces 56, 58, 62, 64.

It should also be appreciated that because the cam surface 54 of the posterior cam 50 includes the concave cam surface 56 and the convex cam surface 58 and the cam surface 34 of the spine 30 includes the convex cam surface 62 and the concave cam surface 64, the contact surface area between the posterior cam 50 and the spine 30 is increased through the flexion range relative to orthopaedic prostheses wherein the posterior cam and/or the spine include planar cam surfaces or cam surfaces having only a concave or convex surface. For example, the contact area between the posterior cam 50 and the spine 30 is increased in early flexion due to the interface between the concave cam surface 56 of the posterior cam 50 and the convex cam surface 62 of the spine 30. Additionally, in late flexion, the contact area between the posterior cam 50 and the spine 30 is increased in later degrees of flexion due to the interface between the convex cam surface 58 of the posterior cam 50 and the concave cam surface 64 of the spine 30. Because the contact between the posterior cam 50 and the spine 30 is spread across a greater contact area, the anterior wear of the spine 30 may also be decreased.

Figure 16:
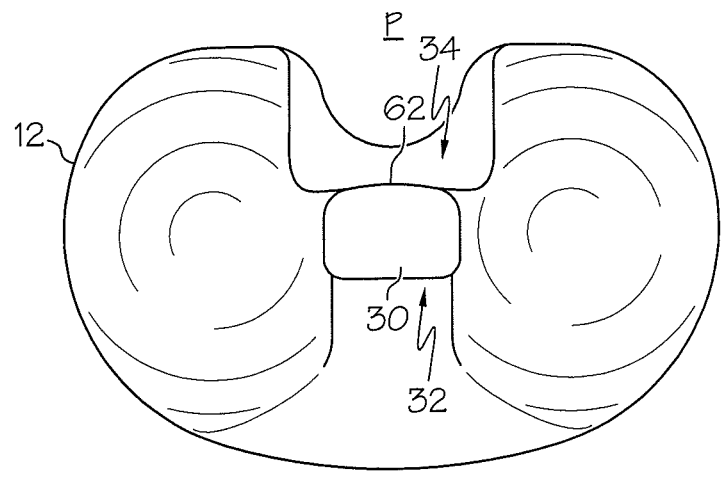
FIG. 16 is a top plan view of another embodiment of the tibial bearing of the orthopaedic prosthesis of FIG. 1.
Figure 17:
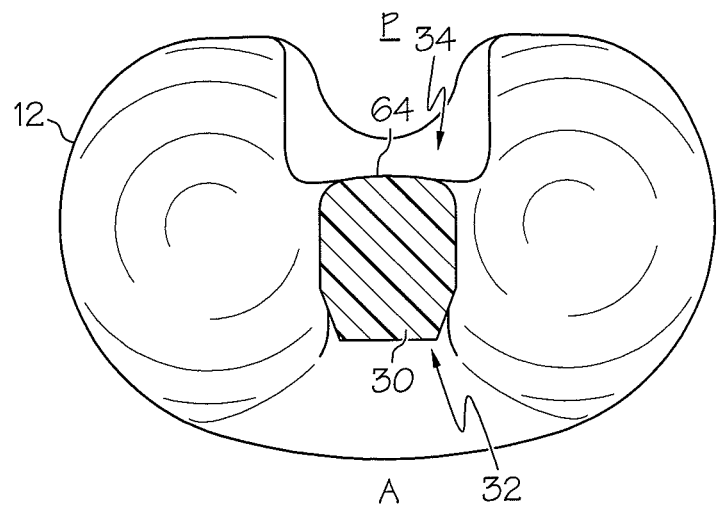
FIG. 17 is a cross-sectional plan view of the tibial bearing of FIG. 16 having a portion of the spine removed.

Referring now to FIGS. 16 and 17, in some embodiments, the posterior side 34 of the spine 30 may also be curved in the transverse plane. That is, each of the superior, convex cam surface 62 and the inferior, concave cam surface 64 may be convex in the transverse plane direction. For example, as illustrated in FIG. 16, the convex cam surface 62 of the spine 30 may be convexly curved in the transverse plane. Additionally, as illustrated in FIG. 17, the concave cam surface 64 of the spine 30 may be convexly curved in the transverse plane. The radius of curvature in the transverse plane of the convex cam surface 62 and the concave cam surface 64 may be substantially equal or different. For example, in some embodiments, the radius of curvature in the transverse plane of the concave cam surface 64 may be greater than the radius of curvature in the transverse plane of the convex cam surface 62. Alternatively, in other embodiments, the radius of curvature in the transverse plane of the convex cam surface 62 may be greater than the radius of curvature in the transverse plane of the concave cam surface 64.

Figure 18:
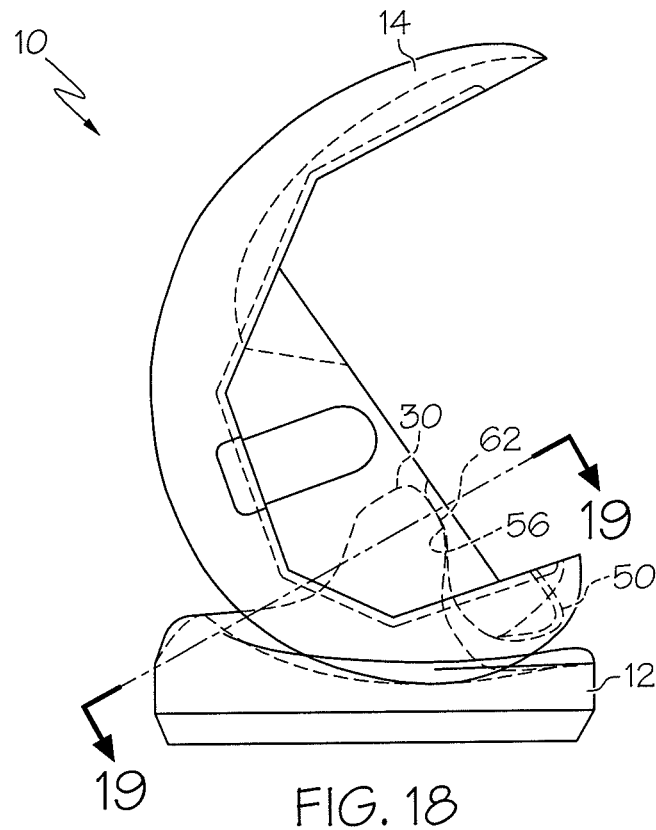
FIG. 18 is a side elevational view of one embodiment of an orthopaedic prosthesis including the tibial bearing of FIG. 16 positioned in an early degree of flexion.
Figure 19:
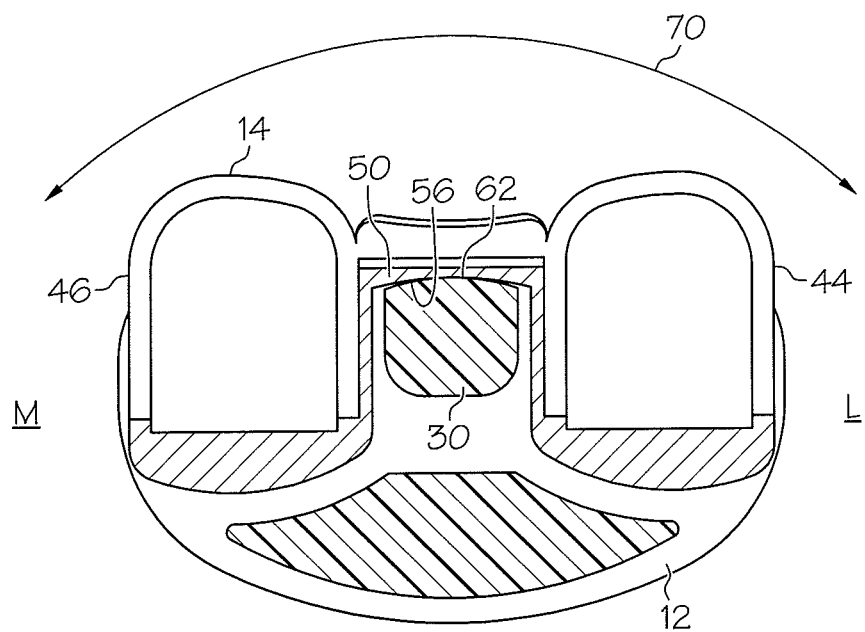
FIG. 19 is a cross-sectional view of the orthopaedic prosthesis of FIG. 18 taken generally along the section line 19-19.

In embodiments wherein the cam surfaces 62, 64 of the spine 30 are curved in the transverse plane, the posterior cam 50 of the femoral component 14 articulates on the cam surfaces 62, 64 in the transverse plane such that the femoral component 14 rotates an amount about the spine 30. For example, as illustrated in FIGS. 18 and 19, when the concave cam surface 56 of the posterior cam 50 is in contact with the convex cam surface 62 of the spine 30 during early flexion, the femoral component 14 may rotate about the spine 30 in a generally medial-lateral direction in the transverse plane as indicated by arrow 70. In such embodiments, the concave cam surface 56 of the posterior cam 50 may be substantially planar in the medial-lateral direction in some embodiments.

Alternatively, similar to the convex cam surface 62 of the spine 30, the concave cam surface 56 of the posterior cam 50 of the femoral component 14 may also be curved in the medial-lateral direction. For example, as illustrated in FIG. 19, the concave cam surface 56 may be concavely curved in the medial-lateral direction. In some embodiments, the radius of curvature in the medial-lateral direction of the concave cam surface 56 may be substantially equal to the radius of curvature in the transverse plane of the convex cam surface 62 of the spine 30. Alternatively, the radius of curvature in the medial-lateral direction of the concave cam surface 56 may be greater or less than the radius of curvature in the transverse plane of the convex cam surface 62. The amount of rotation between the femoral component 14 and the tibial bearing 12 during early flexion may be adjusted based on the radius of curvatures in the transverse plane of the cam surfaces 56, 62. For example, an increased amount of rotation during early flexion of the orthopaedic prosthesis may be obtained by decreasing the radius of curvature in the transverse plane of the convex cam surface 62.

Figure 20:
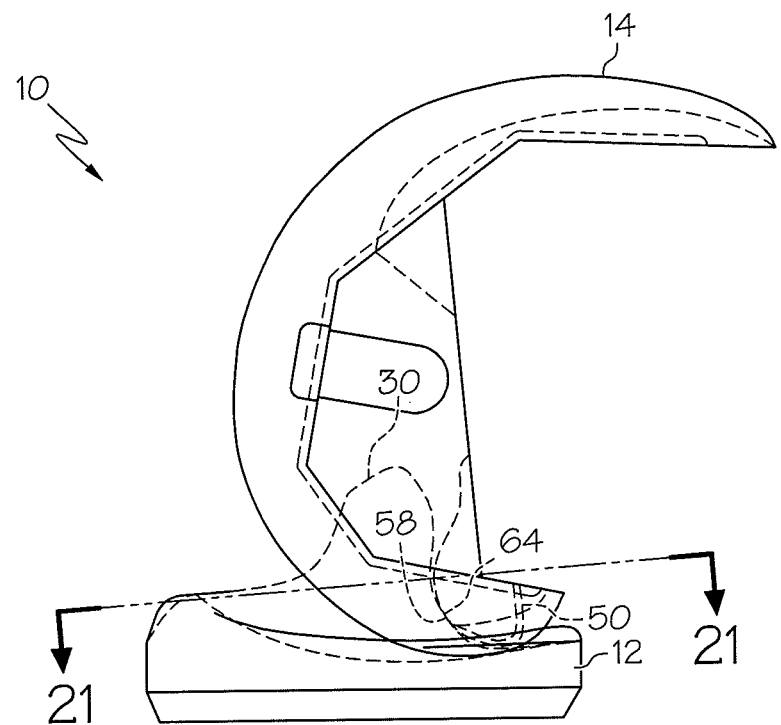
FIG. 20 is a side elevational view of the orthopaedic prosthesis of FIG. 18 positioned in a late degree of flexion.
Figure 21:
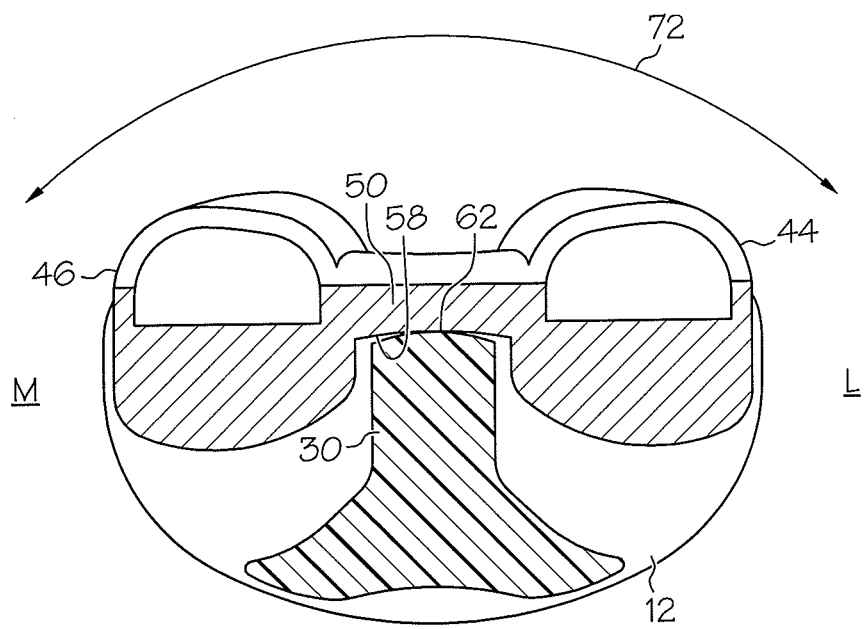
FIG. 21 is a cross-sectional view of the orthopaedic prosthesis of FIG. 20 taken generally along the section line 21-21.

Referring now to FIGS. 20 an 21, when the convex cam surface 58 of the posterior cam 50 is in contact with the concave cam surface 64 of the spine 30 during late flexion, the femoral component 14 may rotate about the spine 30 in a generally medially-laterally direction in the transverse plane as indicated by arrow 72 in some embodiments. In such embodiments, the convex cam surface 58 of the posterior cam 50 may be substantially planar in the medial-lateral direction. Alternatively, similar to the concave cam surface 64 of the spine 30, the convex cam surface 58 of the posterior cam 50 of the femoral component 14 may be curved in the medial-lateral direction. For example, as illustrated in FIG. 21, the convex cam surface 58 may be concavely curved in the medial-lateral direction. In some embodiments, the radius of curvature in the medial-lateral direction of the convex cam surface 58 may be substantially equal to the radius of curvature in the medial-lateral direction of the concave cam surface 64 of the spine 30. Alternatively, the radius of curvature in the medial-lateral direction of the convex cam surface 58 may be greater or slightly less than the radius of curvature in the medial-lateral direction of the concave cam surface 64. As discussed above in regard to early flexion, the amount of rotation between the femoral component 14 and the tibial bearing 12 during late flexion may be adjusted based on the radius of curvatures in the medial-lateral direction of the cam surfaces 58, 64.

As discussed above, the range of late flexion of the illustrative orthopaedic prosthesis 10 is greater than the range of early flexion. However, in other embodiments, the orthopaedic prosthesis 10 may have a range of early flexion that is greater than the range of late flexion. That is, because the range of early and late flexion of the orthopaedic prosthesis is determined, in part, based on the radius of curvature of the cam surface 56, 58, 62, 64, the range of early and late flexion may be adjusted by changing the radius of curvature of the cam surfaces 56, 58, 62, 64 (i.e., the "size" of the cam surfaces). For example, as illustrated in FIGS. 22-28, in another embodiment, the orthopaedic prosthesis 10 may include an early flexion range (i.e., the range at which the concave cam surface of the posterior cam 50 contacts the convex cam surface of the spine 30) that is greater than the late flexion (i.e., the range at which the convex cam surface of the posterior cam 50 contacts the concave cam surface of the spine 30).

Figure 22:
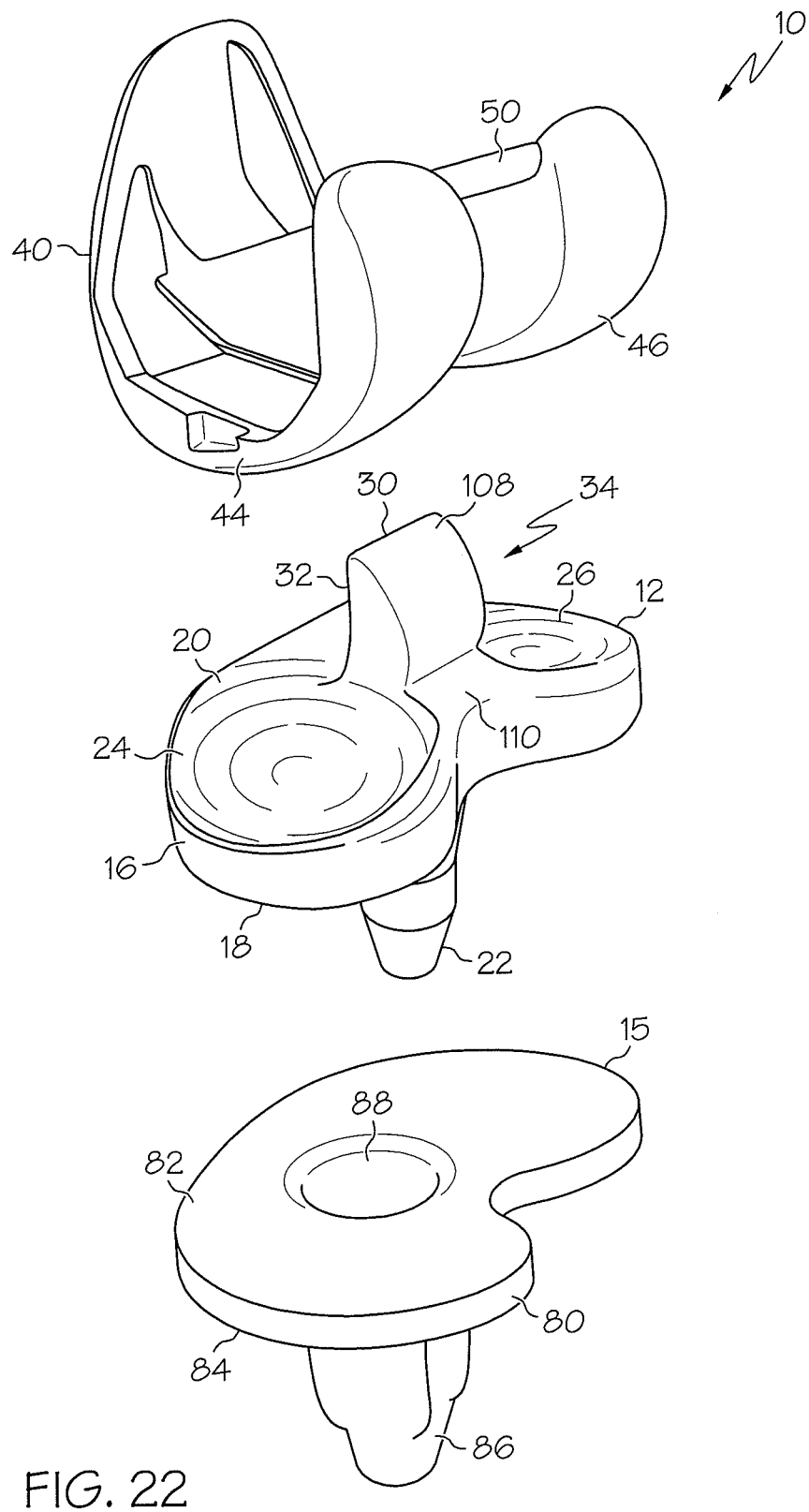
FIG. 22 is an exploded perspective view of another embodiment of an orthopaedic prosthesis.
Figure 23:
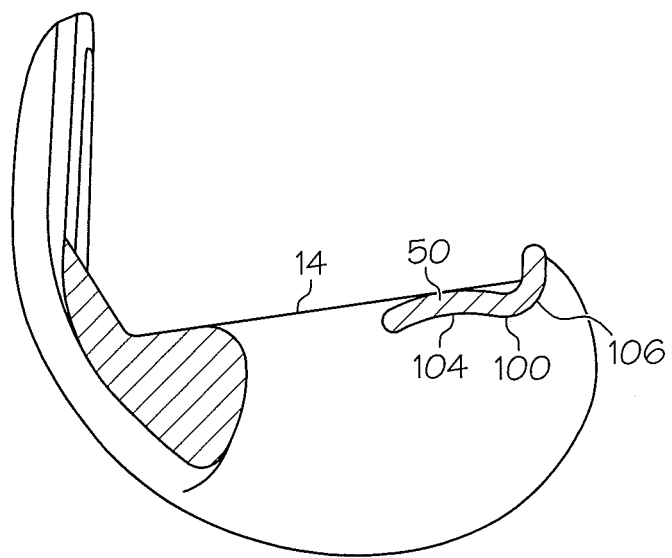
FIG. 23 is a cross-sectional view of one embodiment of a femoral component of the orthopaedic prosthesis of FIG. 22.
Figure 24:
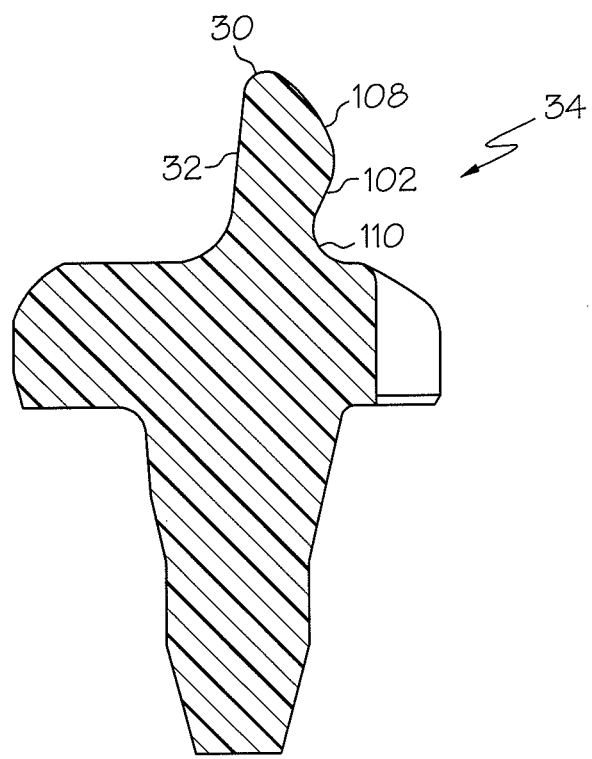
FIG. 24 is a cross-sectional view of one embodiment of a tibial bearing of the orthopaedic prosthesis of FIG. 22.

In such embodiments, as illustrated in FIGS. 22-24, the posterior cam 50 of the femoral component 14 includes a cam surface 100 configured to contact a cam surface 102 of the spine 30 during use. To do so, the cam surface 100 of the posterior cam 50 includes a concave cam surface 104 and a convex cam surface 106. In the illustrative embodiment, the convex cam surface 106 is positioned posteriorly to the concave cam surface 104. The concave cam surface 104 has a radius of curvature substantially larger than the radius of curvature of the convex cam surface 106. As discussed above in regard to the cam surfaces 56, 58, the particular radius of curvature of the cam surfaces 104, 106 (i.e., the "size" of the cam surfaces) may be dependent upon a number of criteria such as the size of the implant, the shape or geometry of the articulating surface of the femoral component 14 and/or the tibial bearing 12, and/or the like. In one particular embodiment, the concave cam surface 104 has a radius of curvature of about 12.7 millimeters and the convex cam surface 106 has a radius curvature of about 6.4 millimeters Similar to the cam surface 100 of the posterior cam 50 of the femoral component 14, the cam surface 102 of the spine 30 includes a convex cam surface 108 and a concave cam surface 110. In the illustrative embodiment, the convex cam surface 108 is positioned superiorly relative to the concave cam surface 110. The convex cam surface 108 has a radius of curvature substantially larger than the radius of curvature of the concave cam surface 110. Again, the particular radius of curvature of the cam surfaces 108, 110 (i.e., the "size" of the cam surfaces) may be dependent upon a number of criteria such as the size of the implant, the patient's anatomy, and/or the like. In one particular embodiment, the convex cam surface 108 has a radius of curvature of about 10.3 millimeters and the concave cam surface 110 has a radius curvature of about 1.00 millimeters.

Figure 25:
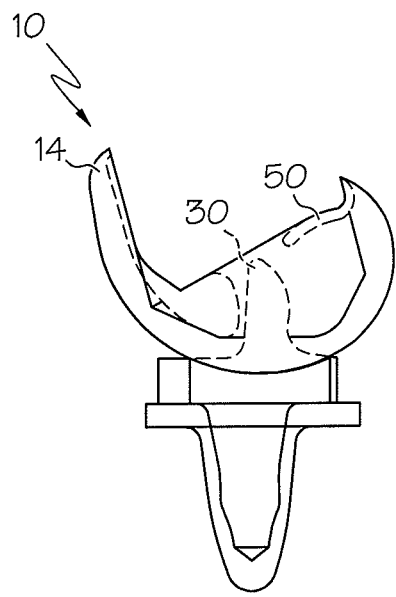
FIGS. 25-28 are side elevational views of the orthopaedic prosthesis of FIG. 22 at various degrees of flexion.
Figure 26:
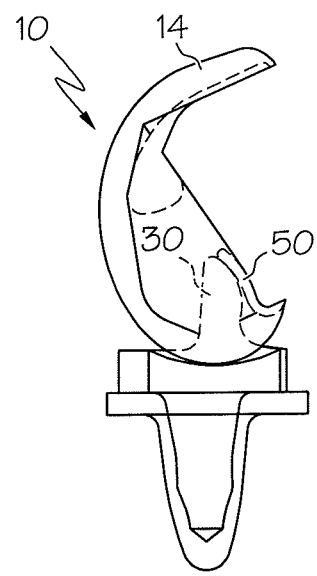
Figure 27:
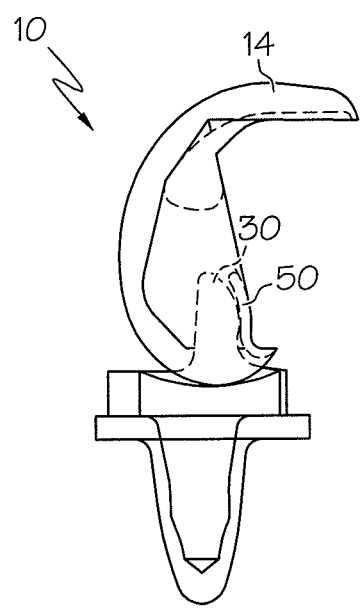
Figure 28:
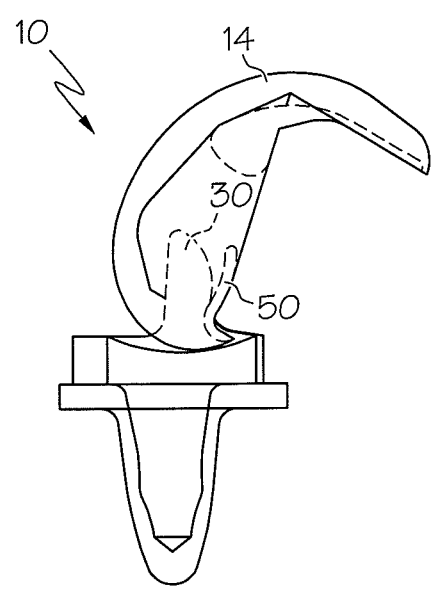

Because radius of curvature of the cam surfaces 104, 108 are greater than the radius of curvature of the cam surfaces 106, 110, the range of early flexion of the embodiment of the orthopaedic prosthesis 10 illustrated in FIGS. 22-28 is greater than the range of late flexion. For example, as shown in FIG. 25, when the orthopaedic prosthesis 10 is in extension or is otherwise not in flexion (e.g., a flexion of about 0 degrees), the posterior cam 50 is not in contact with the spine 30. However, during early flexion as illustrated in FIG. 26, the posterior cam 50 of the femoral component 14 contacts the spine 30 of the tibial bearing 12. That is, during early flexion, the concave cam surface 104 of the posterior cam 50 contacts the convex cam surface 108 of the spine 30. Because the radius of curvature of the cam surfaces 104, 108 are increased, the cams surfaces 104, 108 maintain contact with each other through a larger range of flexion. As such, the range of early flexion of the orthopaedic prosthesis is increased relative to embodiments wherein the radius of curvature of the cam surfaces 104, 108 is decreased. After early flexion, the contact between the posterior cam 50 and the spine 30 transitions from the cam surfaces 104, 108 to the cam surfaces 106, 110. For example, in one embodiment as illustrated in FIG. 27, the contact between the posterior cam 50 and the spine 30 beings transitioning to the cam surfaces 106, 110. At this degree of flexion, initial contact between the convex cam surface 106 of the posterior cam 50 and the concave cam surface 110 of the spine 30 may be established. Subsequently, during late flexion of the orthopaedic prosthesis 10, the convex cam surface 106 maintains contact with the concave cam surface 110 as illustrated in FIG. 28.

Again, it should be appreciated that contact between posterior cam 50 and the spine 30 is maintained throughout the range of early and late flexion. The particular range of early flexion (i.e., the range at which the concave cam surface 104 of the posterior cam 50 contacts the convex cam surface 108 of the spine 30) and late flexion (i.e., the range at which the convex cam surface 106 of the posterior cam 50 contacts the concave cam surface 110 of the spine 30) of the orthopaedic prosthesis 10 may be dependent upon one or more criteria such as the size of the orthopaedic prosthesis 10, the patient's anatomy, or the like. In the illustrative embodiment of FIGS. 22-28, the orthopaedic prosthesis is configured to have an early flexion range of about 50 degrees to about 100 degrees and a late flexion range of about 100 degrees to about 150 degrees, but other ranges of flexion may be used in other embodiments.

It should also be appreciated that because the cam surface 100 of the posterior cam 50 includes the concave cam surface 104 and the convex cam surface 106 and the cam surface 102 of the spine 30 includes the convex cam surface 108 and the concave cam surface 110, the contact surface area between the posterior cam 50 and the spine 30 is increased relative to orthopaedic prostheses wherein the posterior cam and/or the spine include planar cam surfaces or cam surfaces having only a concave or convex surface. In particular, because the concave cam surface 104 of the posterior cam 50 and the convex cam surface 108 of the spine 30 each have large radius of curvatures, the contact area between the posterior cam 50 an the spine 30 is increased during early flexion. Additionally, as discussed above, because the contact between the posterior cam 50 and the spine 30 is spread across a greater contact area, the anterior wear of the spine 30 may also be decreased.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthesis comprising:
a tibial bearing configured to be coupled to a tibial tray, the tibial bearing having a platform and a spine extending upwardly from the platform, the spine having a posterior side including a cam surface having a first section that is convexly curved in the sagittal plane and a second section that is concavely curved in the sagittal plane, and
a femoral component configured to articulate with the tibial bearing, the femoral component including (i) a pair of spaced apart condyles defining an intracondylar notch therebetween, (ii) a posterior cam positioned at a posterior end of the intracondylar notch, the posterior cam including a cam surface having an anterior section that is concavely curved in the sagittal plane and a posterior section that is convexly curved in the sagittal plane, and (iii) an anterior surface positioned at an anterior end of the intracondylar notch such that the intracondylar notch includes an opening defined between the posterior cam and the anterior surface,
wherein (i) during a first range of flexion starting at greater than or equal to 0 degrees of flexion, the posterior cam is spaced apart from the spine, (ii) during a second range of flexion starting at greater than or equal to 50 degrees of flexion, the anterior section of the cam surface of the posterior cam contacts only the first section of the cam surface of the spine and posterior section of the cam surface of the posterior cam is spaced apart from the spine, (iii) during a third range of flexion starting at greater than or equal to 80 degrees of flexion, the anterior section of the cam surface of the posterior cam contacts the first section of the cam surface of the spine and posterior section of the cam surface of the posterior cam contacts the second section of the cam surface of the spine, and (iv) during a fourth range of flexion starting at greater than or equal to 100 degrees of flexion, the anterior section of the cam surface of the posterior cam is spaced apart from the spine and the posterior section of the cam surface of the posterior cam contacts only the second section of the cam surface of the spine.

2. The orthopaedic prosthesis of claim 1, wherein the spine of the tibial bearing and the posterior cam of the femoral component each have a substantially "S"-shaped cross-sectional profile.

3. The orthopaedic prosthesis of claim 1, wherein the first section of the cam surface of the spine of the tibial bearing is located superiorly relative to the second section of the cam surface of the spine.

4. The orthopaedic prosthesis of claim 1, wherein the first range of flexion is about 0 degrees of flexion to about 50 degrees of flexion.

5. The orthopaedic prosthesis of claim 1, wherein the second range of flexion is about 50 degrees of flexion to about 80 degrees of flexion.

6. The orthopaedic prosthesis of claim 1, wherein the third range of flexion is about 80 degrees of flexion to about 100 degrees of flexion.

7. The orthopaedic prosthesis of claim 1, wherein the first section of the spine of the tibial bearing is defined by a first radius of curvature and the second section of the spine is defined by a second radius of curvature different from the first radius of curvature.

8. The orthopaedic prosthesis of claim 1, wherein the anterior section the posterior cam of the femoral component is defined by a first radius of curvature and the posterior section of the posterior cam is defined by a second radius of curvature different from the first radius of curvature.

9. The orthopaedic prosthesis of claim 1, wherein:
the anterior section of the cam surface of the posterior cam is a first anterior section, and
the cam surface of the posterior cam includes a second anterior section positioned anterior of the first anterior section, the second anterior section being convexly curved in the sagittal plane.

10. An orthopaedic prosthesis comprising:
a tibial bearing configured to be coupled to a tibial tray, the tibial bearing having a platform including a medial bearing surface and a lateral bearing surface and a spine extending upwardly from the platform between the medial bearing surface and the lateral bearing surface, the spine having a posterior side including a cam surface having a first section that is convexly curved in the sagittal plane and convexly curved in the transverse plane, and a second section that is concavely curved in the sagittal plane and convexly curved in the transverse plane, and
a femoral component configured to articulate with the tibial bearing, the femoral component including (i) a pair of spaced apart condyles defining an intracondylar notch therebetween, (ii) a posterior cam positioned at a posterior end of the intracondylar notch, the posterior cam including a cam surface having an anterior section that is concavely curved in the sagittal plane and a posterior section that is convexly curved in the sagittal plane, and (iii) an anterior surface positioned at an anterior end of the intracondylar notch such that the intracondylar notch includes an opening defined between the posterior cam and the anterior surface, wherein (i) at a flexion angle of about 0 degrees of flexion, the posterior cam is disengaged from the spine, (ii) only the anterior section of the cam surface of the posterior cam contacts the first section of the cam surface of the spine during a first range of flexion starting at a flexion angle of at least about 50 degrees, and (iii) contact between the posterior cam and the spine transitions to contact between the posterior section of the cam surface of the posterior cam and the second section of the cam surface of the spine in a second range of flexion starting at a flexion angle of at least 80 degrees, wherein the first section of the cam surface of the spine of the tibial bearing is located superiorly relative to the second section of the cam surface of the spine, wherein the spine of the tibial bearing and the posterior cam of the femoral component each have a substantially "S"-shaped cross-sectional profile in the sagittal plane.

11. The orthopaedic knee joint prosthesis of claim 10, wherein the first range of flexion is about 50 degrees of flexion to about 80 degrees of flexion and the second range of flexion is about 80 degrees of flexion to about 150 degrees of flexion.

12. The orthopaedic prosthesis of claim 10, wherein the anterior section of the cam surface of the posterior cam is a first anterior section, and the cam surface of the posterior cam includes a second anterior section positioned anterior of the first anterior section, the second anterior section being convexly curved in the sagittal plane.

* * * * *